United States Patent [19]

Drent

[11] Patent Number: 4,536,354
[45] Date of Patent: Aug. 20, 1985

[54] PROCESS FOR THE PREPARATION OF CARBOXYLIC ANHYDRIDES

[75] Inventor: Eit Drent, Amsterdam, Netherlands

[73] Assignee: Shell Oil Company, Houston, Tex.

[21] Appl. No.: 560,094

[22] Filed: Dec. 12, 1983

[30] Foreign Application Priority Data

Dec. 17, 1982 [NL] Netherlands ............... 8204883

[51] Int. Cl.³ ........................................... C07C 51/12
[52] U.S. Cl. ........................................ 260/549; 260/546
[58] Field of Search ................................. 260/549, 546

[56] References Cited

U.S. PATENT DOCUMENTS

| | | | |
|---|---|---|---|
| 3,725,305 | 4/1973 | Wilkinson | 502/153 |
| 4,190,729 | 2/1980 | Forster | 560/232 |
| 4,239,698 | 12/1980 | Isshiki et al. | 260/549 |
| 4,273,936 | 6/1981 | Fiato et al. | 562/522 |
| 4,335,059 | 6/1982 | Rizkalla | 260/549 |

FOREIGN PATENT DOCUMENTS 0050084 4/1982 European Pat. Off. .

OTHER PUBLICATIONS

Kosolapoff, Gennady M. Organophosphorus Compounds (1958) p. 23, John Wiley & Sons, publ.

*Primary Examiner*—Natalie Trousof
*Assistant Examiner*—Hendriksen L.
*Attorney, Agent, or Firm*—Ronald R. Reper

[57] ABSTRACT

A process is disclosed for preparing carboxylic acid anhydrides by reacting certain esters or ethers with carbon monoxide in the presence of a nickel catalyst, a source of iodide and/or bromide and conventional promoters, which process is improved by the use as co-promoters of a compound selected from compounds of the formula

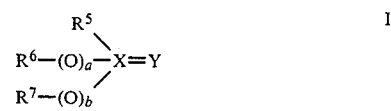

in which X represents phosphorus, arsenic or antimony and Y represents oxygen, sulphur or selenium, and a and b are O or 1 and $R^5$ represents hydrogen or an optionally substituted hydrocarbon group and $R^6$ and $R^7$ represent an optionally substituted hydrocarbon group; compounds wherein a and b are O and $R^6$ and $R^7$ form a heterocyclic group with X and $R^5$ represents hydrogen or an optionally substituted hydrocarbon group; and complexes of compounds of formula I with any of a hydrocarbon iodide or bromide, an acyl iodide or bromide, or hydrogen iodide or hydrogen bromide.

19 Claims, No Drawings

PROCESS FOR THE PREPARATION OF CARBOXYLIC ANHYDRIDES

BACKGROUND OF THE INVENTION

The invention relates to a process for the preparation of carboxylic anhydrides by carbonylation of carboxylic esters or of ethers. The invention relates in particular to the preparation of acetic anhydride from methyl acetate or dimethyl ether.

British Patent Specification No. 1,538,783 describes a process for the preparation of carboxylic anhydrides by carbonylation of a carboxylic ester or of an ether in the presence of a group VIII noble-metal compound, an iodide or bromide, a promoter and an organic nitrogen or phosphorus compound in which the nitrogen or phosphorus is trivalent. Group VIII noble metals are, however, expensive and there is a need for a process in which cheaper catalysts, such as, for instance, nickel catalysts, can be used with the conversion desired being nonetheless achieved under moderate reaction conditions at a rate suitable for use on a commercial scale. Carbonylation of esters or ethers in the presence of nickel complexes has been described in U.S. Pat. No. 2,729,651. However, the reaction is carried out under very high pressures.

As appears from U.S. Pat. No. 4,002,678, it is possible to employ lower pressures by carrying out the carbonylation in the presence of an iodide or bromide, an organic nitrogen or phosphorus compound in which the nitrogen or phosphorus is trivalent and a catalyst comprising both a nickel and a chromium component. In most examples, a reaction temperature of 150°–155° C. is used.

European Patent Specification No. 48,210 points out that the reaction rate of the process according to U.S. Pat. No. 4,002,678 is low and a process is described in which carbonylation is carried out in the presence of a nickel catalyst, an alkyl or acyl iodide, a sulphone as solvent and an alkali metal salt, alkaline earth metal salt, quaternary ammonium iodide or quaternary phosphonium iodide as co-catalyst. The reaction is, however, effected at a considerably elevated temperature of at least 180° C. According to Example 9, use of an elevated temperature appears to be essential for a reasonable conversion rate to be achieved. In that example, a mere 5% conversion of the methyl acetate is achieved at a temperature of 160° C.

European Patent Specification No. 55,622 likewise describes a process for the preparation of acetic anhydride by carbonylation of methyl acetate or dimethyl ether, the aim being to cause the reaction to proceed at as high a rate as possible. The carbonylation is effected in the presence of nickel or a nickel compound, an iodide or bromide, an organic nitrogen compound and a co-catalyst comprising one or more compounds of metals in groups IA, IIA, IIIA and IVA of the "Periodic System". (The "Periodic System" to which reference is made in this specification is reproduced in the "Handbook of Chemistry and Physics" 45th edition 1964–1965, p. B). With this process too, a temperature of at least 170° C. and usually 180°–200° C. is used.

It has now been found that, in the preparation of carboxylic anhydrides by carbonylation of an ester or ether in the presence of a nickel catalyst, an iodide and/or bromide source and a co-promoter (or co-catalyst), a further rise of the reaction rate can be achieved by carrying out the reaction in the presence of a compound having the formula I stated hereinafter as promoter. Said rise also occurs in the presence of sulphones or of the co-promoters such as quaternary ammonium iodides and alkali metal compounds recommended in European Patent Specifications Nos. 48,210 and 55,622 for increasing the reaction rate. Even at relatively low temperatures, such as for example 165° C., the compound having the formula I increases the reaction rate to a considerable degree. This is, inter alia, of interest because catalyst stability is generally greater at lower temperatures. The enhancement of reaction rate also occurs if only small quantities of nickel catalyst and/or iodide or bromide are used and if there is no (additional) solvent. When the process is effected on a commercial scale, it is naturally an important advantage if the quantity of catalyst to be recovered and the quantities of iodide and/or bromide, such as methyl iodide, and solvent can be kept low. If the examples stated hereinafter are consequently expressed in g carboxylic anhydride/g Ni/g I or Br/hour. This mode of expression is, moreover, more correct because reaction rate is generally directly proportional to both the quantity of Ni and the quantity of I or Br present in the reaction mixture. With the process according to the invention, very high reaction rates of, for example, 20 g carboxylic anhydride/g Ni/g I/hour can be achieved.

SUMMARY OF THE INVENTION

The invention relates to a process for the preparation of a carboxylic anhydride by reacting under virtually water-free conditions an ester having the formula $R^1COOCH_2R^2$ or an ether having the formula $R^3OR^4$ in which $R^1$, $R^3$ and $R^4$ represent substituted or non-substituted hydrocarbon groups and $R^2$ represents hydrogen or a substituted or non-substituted hydrocarbon group with carbon monoxide in the presence of a nickel catalyst, an iodide and/or bromide source and at least one co-promoter, characterized in that the reaction is carried out in the presence of a compound having the formula

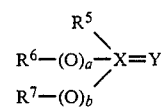

in which X represents phosphorus, arsenic or antimony and Y oxygen, sulphur or selenium and a and b are 0 or 1 and $R^5$ represents hydrogen or a substituted or non-substituted hydrocarbon group and $R^6$ and $R^7$ represent a substituted or non-substituted hydrocarbon group, or a and b are 0 and $R^6$ and $R^7$ form a heterocyclic group with X and $R^5$ represents hydrogen or a substituted or non-substituted hydrocarbon group, or in the presence of a complex of a compound having the formula I with a compound selected from the group consisting of hydrocarbon iodide or bromide, an acyl iodide or bromide or HI or HBr.

DESCRIPTION OF PREFERRED EMBODIMENTS

Hydrocarbon groups $R^1$, $R^2$, $R^3$ and $R^4$ may be alkyl, cycloalkyl, aryl, alkaryl or aralkyl groups with preferably not more than 20 carbon atoms. Alkyl groups with 1–12, in particular 1–4 carbon atoms are particularly preferred. The hydrocarbon groups may be optionally substituted with one or more substituents that are inert under the reaction conditions, for example halogen atoms. Methyl acetate and dimethyl ether are highly suitable starting materials.

As nickel catalyst, metallic nickel such as nickel powder or Raney nickel or an inorganic or organic nickel compound or a nickel complex can be used. Typical examples of suitable nickel compounds are nickel chloride, bromide, iodide, hydride, oxide, hydroxide or carbonate or nickel salts with carboxylic acids having 1–20 carbon atoms such as, for example, nickel acetate, nickel propionate, nickel laurate or nickel benzoate or alkoxides or nickel such as, for example, the methoxide or phenoxide. Typical examples of suitable nickel complexes are nickel tetracarbonyl, nickel acetylacetonate and nickel dicarbonylbistriphenylphosphine, quaternary ammonium nickel halides, such as tetramethylammonium nickel iodide and complexes of nickel salts with quaternary ammonium salts and alkyl halides, for example an $NiCl_2/(C_4H_9)_4NI/CH_3I$ complex.

The quantity of nickel catalyst preferably lies between $1.5 \times 10^{-5}$ and $1.5 \times 10^{-1}$, in particular between $1.5 \times 10^{-4}$ and $0.3 \times 10^{-1}$ gram-atoms Ni per mol ester or ether. Very good results are, for example, achieved with $1.5 \times 10^{-3}$ gram-atoms Ni per mol ester or ether.

The iodide and/or bromide source can, for instance, be elementary iodine or bromine, or hydrogen iodide or hydrogen bromide or an $R^8I$, $R^8Br$, $R^8COI$ or $R^8COBr$ compound, in which $R^8$ represents an alkyl group optionally substituted with bromine or iodine or an aralkyl group with preferably not more than 12 carbon atoms. $R^8I$ or $R^8COI$ compounds in which $R^8$ represents an alkyl group with 1–4 carbon atoms, in particular methyl iodide, are particularly preferred as iodide source. Specific examples of other suitable iodide and/or bromide sources are $CH_3Br$, $C_2H_5I$, $C_4H_9I$, $C_8H_{17}I$, $CH_2I_2$, $C_2H_4I_2$, $CH_2IBr$, $CHI_3$ and $C_2H_4IBr$.

Metal iodides or bromides can equally be used as iodide or bromide source. Typical examples of such compounds are iodides and bromides of metals in group I of the "Periodic System" such as lithium, sodium, potassium, cesium, rubidium and copper, and iodides and bromides of metals in group II such as calcium, magnesium and zinc, and of vanadium, chromium and manganese. Mixtures of iodides and bromides can also be used. If the catalyst comprises an iodine or bromine compound of nickel, such as, for example, $NiI_2$ or $NiBr_2$, the latter can likewise act as iodine or bromide source. Finally, the co-promoter can also act as iodide or bromide source if it consists of an iodine or bromine-containing compound.

The quantity of iodide and/or bromide source, that is to say the total number of gram-atoms I and/or Br present in the reaction mixture, lies generally between 0.1 and 1,000, preferably between 1 and 500 and particularly between 10 and 300 gram-atoms I and/or Br per gram-atom Ni. Very good results are, for instance, achieved with 30 gram-atoms I per gram-atom Ni.

It is known from European Patent Specification No.55,622 that diverse compounds can be used as co-promoter (co-catalyst) in the carbonylation of methyl acetate or dimethyl ether in the presence of a nickel catalyst. In the process according to the invention, one or more compounds of metals in groups IA, IIA, IIIA, IVA, IVB, VB, VIB and VIIB and/or of the non-noble metals in group VIII of the "Periodic System" and/or of metals in the lanthanides group and/or one or more organophosphorus compounds and/or organonitrogen compounds in which the phosphorus or nitrogen is trivalent, and/or salts of said phosphorus or nitrogen compounds, may suitably be used as co-promoter.

Typical examples of metal compounds that can be used as copromoter are compounds of potassium, rubidium, cesium, magnesium, calcium, strontium, aluminum, molybdenum and cobalt. Very good results are achieved with compounds of lithium, sodium, didymium (for a description of that metal see U.S. Pat. No. 3,758,417), zirconium, vanadium, chromium, tungsten, manganese, iron and tin. Suitable compounds are, for instance, the oxides, hydroxides, hydrides, alkyls, alkoxides, salts, including the enol salts, and complex compounds of said metals. Usable salts are, for example, the chlorides, bromides, iodides, oxychlorides, sulphates, phosphates, phosphites, nitrates and salts of carboxylic acids such as acetates, butyrates and laurates. The use of iodides and bromides has the advantage that said compounds can at the same time act as iodide or bromide source. Iodides and bromides of group IA metals, in particular of sodium and lithium are preferred for use as co-promoters.

Carbonyl compounds, for instance of the non-noble metals in group VIII, such as $Co_2(CO)_8$ are suitable complex compounds. Carbonyl compounds of group VIB metals, such as $Cr(CO)_6$ and $W(CO)_6$ are preferred for use as co-promoters. Moreover, salts of carboxylic acids corresponding to the anhydride to be prepared, in particular salts of metals in groups IA, IIA and VIIB and of the non-noble metals in group VIII, are preferred.

The quantity of metal compounds used as co-promoter lies generally between 0.1 and 100, particularly between 0.5 and 50 mol per gram-atom nickel.

Organophosphorus compounds in which the phosphorus is trivalent, suitable for use as co-promoter, are alkyl-, cycloalkyl-, aryl- and aralkylphosphines preferably having not more than 30 carbon atoms, such as, for instance trimethylphosphine, tributylphosphine, triphenylphosphine, phosphines containing two or more phosphine groups such as, for instance, tetraphenyldimethylenediphosphine, heterocyclic phosphorus compounds such as, for instance, 1-phenylphospholane and 1-phenylphosphorinane and phosphites such as, for instance, trialkyl- and triarylphosphites such as triphenylphosphites. Trivalent arsenic or antimony compounds corresponding to the aforesaid phosphines are equally serviceable.

Organonitrogen compounds in which the nitrogen is trivalent, suitable for use as co-promoter, are alkyl-, cycloalkyl-, aryl- and aralkylamines preferably having not more than 30 carbon atoms such as, for instance, monomethylamine, dimethylamine, trimethylamine, diethylamine, triethylamine, tributylamine, aniline, dimethylaniline and amines containing two or more amino groups such as, for instance, tetramethylenediamine. Nitriles, such as acetonitrile and benzonitrile and heterocyclic amines preferably having not more than 14 carbon atoms such as, for instance, pyrrole, pyrrolidine, pyridine, piperidine, pyrimidine, pyrazine, benzotriazole, 1,10-phenanthroline and morpholine, optionally substituted with one or more alkyl groups, are equally usable. Pyridine and alkylsubstituted pyridines, such as, for instance, alpha-picoline, are preferred. Amides, including the lactams, preferably having not more than 14 carbon atoms, are highly suitable co-promoters. Typical examples of suitable amides are dimethyl acetamide and methylphenylacetamide. N-methylpyrrolidone is a particularly suitable co-promoter.

Finally, salts of the aforesaid trivalent phosphorus or nitrogen compounds can also be used as co-promoter. Particular mention may here be made of the salts that can be obtained by reacting the trivalent phosphorus or nitrogen compounds, in particular phosphines or amines, with HBr, HI or alkyl halides such as, for instance, $CH_3I$, $C_2H_5I$, $C_4H_9I$, $C_2H_5Br$ or $C_4H_9Br$. Such salts can also arise in situ, for example by a phosphine or amine reacting with alkyl iodides present in the reaction mixture. Specific examples of salts that can be used as co-promoter are triphenylphosphonium iodide, methyltriphenylphosphonium iodide, ethyltriphenylphosphonium bromide, tetramethylammonium iodide, tetrapropylammonium iodide, tetraisopropylammonium iodide, methyltributylammonium iodide, tetrabutylammonium bromide and tetrabutylammonium iodide. Tetra-alkylammonium iodides having more than 2 carbon atoms in the alkyl groups are preferred.

The quantity of organophosphorus compound or organonitrogen compound in which the phosphorus or nitrogen is trivalent, or the quantity of salt of such a compound, lies generally between 0.1 and 100, in particular between 1 and 20 mol per gram-atom Ni.

As hereinbefore mentioned, in the process according to the invention a compound having the formula I is used as promoter. The hydrocarbon groups $R^5$, $R^6$ and $R^7$ may be alkyl, cycloalkyl, aryl, aralkyl or alkaryl groups preferably containing not more than 30 carbon atoms and are optionally substituted with one or more substituents, such as, for instance, halogen atoms or a $R^9R^{10'}X=Y$ group in which X and Y have the hereinbefore stated meaning and $R^9$ and $R^{10}$ represent a substituted or non-substituted hydrocarbon group. If $R^6$ and $R^7$ form a heterocyclic group with X, said group preferably contains not more than 20 carbon atoms. Specific examples are the phospholane, phosphorinane and phosphohepane groups in which the $R^6$ and $R^7$ groups together form an alkylene group having 4, 5 or 6 carbon atoms, respectively, and the 9-phosphabicyclo[4.2.1]nonane and the 9-phosphabicyclo[3.3.1]nonane groups. Said heterocyclic groups may, for instance, be substituted with hydrocarbon groups.

Compounds having the formula I in which a and b are 0, X is phosphorus and Y oxygen or sulphur and $R^5$, $R^6$ and $R^7$ represent alkyl groups with 1-12 carbon atoms or cycloalkyl, aryl, aralkyl or alkaryl groups with 5-12 carbon atoms are preferred. Particular preference is given to compounds having the general formula I in which Y represents oxygen and $R^5$, $R^6$ and $R^7$ alkyl groups with 1-12 carbon atoms or phenyl groups.

Specific examples of compounds having the formula I are the oxides, sulphides or selenides of secondary and tertiary phosphines, arsines and stibines such as trimethylphosphine oxide, diethylphosphine oxide, triethylphosphine oxide, tri-n-butylphosphine oxide, trioctylphosphine oxide, diphenylphosphine oxide, tri-p-tolylphosphine oxide, tricyclohexylphosphine oxide, diphenylethylphosphine oxide, tri(1-naphthyl)phosphine oxide, trimethylphosphine sulphide, tri-4-chlorophenylphosphine sulphide, triphenylphosphine sulphide, tricyclohexylphosphine sulphide, tri-n-butylphosphine sulphide, triphenylphosphine selenide, tris(1-naphthyl)phosphine selenide, triethylarsine oxide, triphenylstibine oxide and triphenylarsine sulphide. Triphenylphosphine sulphide and, in particular, triphenylphosphine oxide are highly suitable promoters. Specific examples of compounds having a heterocyclic phosphorus-containing group are 1-phenylphospholane oxide, 1-phenylphosphorinane oxide, 9-phenyl-9-phosphabicyclo[4.2.1]nonane oxide, 9-phenyl-9-phosphabicyclo[3.3.1]nonane oxide, 9-phenyl-9-phosphabicyclo[3.3.1]nonane oxide, 9-eicosyl-9-phosphabicyclo[4.2.1]nonane oxide, 9-eicosyl-9-phosphabicyclo[3.3.1]nonane oxide, 1-phenylphospholane sulphide, 1-phenylphosphorinane sulphide.

Typical examples of compounds having the general formula I in which a and b are 1 are the alkyl, cycloalkyl, aryl, aralkyl or alkaryl esters of phosphonic and phosphinic acids and the analogues of said compounds in which the doubly bonded oxygen atom has been replaced by a sulphur or selenium atom and/or the phosphorus atom by an arsenic or antimony atom. Specific examples of such compounds are dimethyl methylphosphonate, diethyl methylphosphonate, diphenyl methylphosphonate, methyl dimethylphosphinate and phenyl dimethylphosphinate.

Specific examples of compounds having formula I in which one or more of the $R^5$, $R^6$ and $R^7$ groups are substituted with a $R^9R^{10'}X=Y$ group are the compounds:

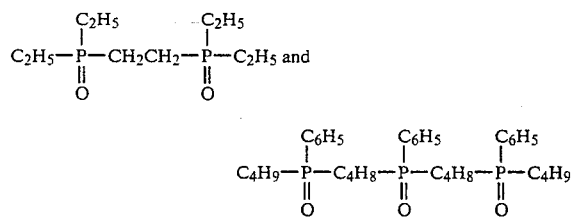

Finally, in the process according to the invention, complexes can be used that are obtained by reacting a compound having the formula I with a hydrocarbon iodide or bromide such as, for instance, $CH_3I$, an acyl iodide or bromide, or HI or HBr.

Typical examples of such complexes are: $[(C_6H_5)_3PO-H-OP(C_6H_5)_3]^+I_3^-$ or $[(C_2H_5) AsO-H-OAs(C_2H_5)]^+I^-$. It has been found that such complexes, which can probably also arise in situ by reaction of the compound having the formula I and iodine or bromide compounds present in the reaction mixture are highly active promoters in the process according to the invention.

If, in the compound having the formula I, X represents phosphorus and Y oxygen and a and b are 0, said compound can be caused to arise in situ by using, instead of the relevant compound having the general formula I, the corresponding phosphine and by effecting the reaction in the presence of molecular oxygen or hydrogen peroxide.

The quantity of compound having the formula I used in the process according to the invention as promoter can vary between wide limits, for example between 0.01 and 200 mol per gram-atom Ni. Preferably 0.1-100 and in particular 1-50 mol per gram-atom Ni are used.

The process according to the invention can generally be carried our at temperatures between 200° and 300° C. Preferably a temperature between 100° and 200° C. and in particular one between 140° and 185° C. is used. The reaction is generally effected at a total pressure of 1-100 bar, preferably 10-100 bar. The partial CO pressure preferably lies between 0.5 and 50 bar. High pressures up to, for instance, 1000 bar may be applied if so desired, but are not generally attractive for technical and economic reasons.

The carbon monoxide used in the process according to the invention may be optionally mixed with other gases such as, for instance, carbon dioxide, methane, nitrogen, noble gases or hydrogen. By using compounds having the formula I as promoter, relatively large quantities of hydrogen may be present without the formation of by-products such as ethylidene diacetate being encouraged. A CO and $H_2$ mixture with a molar ratio of 1:1 is highly serviceable in the process according to the invention.

The process is carried out under virtually water-free conditions because, inter alia, water could cause hydrolysis of the carboxylic anhydride formed. The presence of small quantities of water, such as occur in the commercial chemicals used in the process, for instance in the form of crystallization water is, however, permissible. The reaction mixture contains preferably not more than 2, in particular not more than 0.2%w water.

The process can be carried out in the liquid or gaseous phase, preference being given to the liquid phase. The use of an (additional) solvent is not usually necessary because the ester $R^1COOCH_2R^2$ or the ether $R^2OR^4$ acts as solvent to a sufficient degree. Other reaction mixture constituents, for instance and iodide source such as $CH_3I$, a co-promoter such as triphenylphosphine or N-methylpyrrolidone or the carboxylic anhydride formed can help to keep the reaction mixture homogeneous. If desired, additional quantities of those compounds may be added to the reaction mixture. Suitable (additional) solvents are, for instance, acetic acid, propionic acid, methyl acetate, butyrolactone, dimethyl ether, diethyl ether, acetic anhydride, methyl-t-butyl ether, diglyme, tetraglyme, tetrahydrofuran, 4-dioxane, 1,3-dioxane, the dioxalanes, dimethyl sulphone, diethyl sulphone, methylethyl sulphone, methylbutyl sulphone, sulfolane, 2-methyl sulfolane, 3-methyl sulfolane, 2-methyl-4-butyl sulfolane, dimethyl sulphoxide, diethyl sulphoxide and N-methylpyrrolidone.

The process may be carried out continuously, semi-continuously or batchwise. The reaction mixture obtained can be upgraded with the aid of known techniques such as, for instance, fractional distillation. The process may, moreover, be integrated with existing processes for the preparation of the starting materials or for the further processing of the carboxylic anhydride obtained.

EXAMPLE I

A 300 ml magnetically stirred Hastelloy C autoclave ("Hastelloy" is a trade mark) was charged with 50 ml methyl acetate (657 mmol) and the compounds given in Table A in the stated quantities. The autoclave was flushed with carbon monoxide and filled with a pressurized mixture of carbon monoxide and hydrogen. The partial CO and $H_2$ pressures were each 20 bar. The autoclave was subsequently heated to 165° C. and kept at that temperature for 3.5 hours. The reaction mixture was cooled down and analyzed with the aid of gas-liquid chromatography. The quantity of acetic anhydride ($Ac_2O$) was determined and the reaction rate, expressed in g $Ac_2O$/g Ni/g I/hour, calculated. The results are summarized in Table A.

Tests 1-5 are not in accordance with the invention. In tests 1 and 3-5 the promoter is lacking which, according to the invention, must be used (fourth column of Table A) and in test 2 the co-promoter is lacking whose presence, as the test indicates, is equally essential. The substantial effect that triphenylphosphine oxide or the reaction product of that compound with HI has on the reaction rate is evidenced by comparison of tests 1-5 with tests 6-13. It is also evident that the enhancing effect of triphenyl phosphine oxide occurs when it is used in conjunction with co-promoters of diverse types. Comparison of tests 3 and 5 with, for instance, tests 9, 12 and 13 shows that triphenylphosphine or a quaternary compound thereof with $C_2H_5I$ increase the reaction rate far less than triphenylphosphine oxide does. Furthermore, tests 4, 6 and 11 demonstrate that the promoter activity, in itself not inconsiderable of tetrabutylammonium iodide can be further increased by addition of triphenylphosphine oxide.

EXAMPLE II

In the manner described in Example I, methyl acetate was carbonylated at 165° C. in the presence of 1 mmol $NiCl_2.6H_2O$, varying quantities of $CH_3I$ and various promoters and co-promoters. The specific data are given in Table B. $P_{CO}$ and $P_{H2}$ are the partial CO and $H_2$ pressures in the autoclave before the latter was heated. Tests 1-3 are not in accordance with the invention. In test 1 the co-promoter is lacking and in tests 2 and 3 the promoter. The intense promoter activity of triphenylphosphine oxide and trioctylphosphine oxide, if used in conjunction with a co-promoter, is evidenced by comparison of tests 4-7 with test 1.

EXAMPLE III

In the manner described in Example I, 45 ml (591 mmol) of methyl acetate were carbonylated at 180° C. in the presence of 1 mmol $NiCl_2.6H_2O$ and varying quantities of $CH_3I$, N-methylpyrrolidone, $LiI.2H_2O$ and triphenylphosphine oxide. The reaction time was 2 hours. The specific data are stated in Table C. The partial CO and $H_2$ pressures in the autoclave before the latter was heated measured 30 and 15 bar, respectively. The intense promoter activity of triphenylphosphine oxide is made evident by comparison of tests 2-4 with test 1 (blank).

TABLE A

| Test No. | Catalyst (mmol) | $CH_3I$ (mmol) | Promoter (mmol) | Co-promoter(mmol) | $gAc_2O$/g Ni/g I/hour |
|---|---|---|---|---|---|
| 1 | $NiCl_2.6H_2O$ (1) | 90 | — | $Cr(CO)_6$ (1) | <0.01 |
| 2 | $NiCl_2.6H_2O$ (1) | 90 | $(C_6H_5)_3P=O$ (4) | — | <0.01 |
| 3 | $NiCl_2.6H_2O$ (1) | 90 | — | $Cr(CO)_6$ (1) $(C_6H_5)_3PC_2H_5I$ (2) | 0.24 |
| 4 | $NiCl_2.6H_2O$ (8) | 90 | — | $(C_4H_9)_4NI$ (10) | 0.44 |
| 5 | $NiCl_2.6H_2O$ (1) | 90 | — | $W(CO)_6$ (1) $(C_6H_5)_3P$ (5) | 0.1 |
| 6 | $NiCl_2.6H_2O$ (8) | 90 | $(C_6H_5)_3P=O$ (8) | $(C_4H_9)_4NI$ (10) | 0.70 |

TABLE A-continued

| Test No. | Catalyst (mmol) | CH$_3$I (mmol) | Promoter (mmol) | Co-promoter(mmol) | gAc$_2$O/g Ni/g I/hour |
|---|---|---|---|---|---|
| 7 | NiCl$_2$.6H$_2$O (4) | 90 | (C$_6$H$_5$)$_3$P=O (4) | (C$_4$H$_9$)$_4$NI (10) Mn(CH$_3$COO)$_2$ (8) | 0.83 |
| 8 | NiCl$_2$.6H$_2$O (1) | 90 | [(C$_6$H$_5$)$_3$P=O]$_2$HI$_3$ (2) | Cr(CO)$_6$ (1) | 2.15 |
| 9 | NiCl$_2$.6H$_2$O (1) | 90 | (C$_6$H$_5$)$_3$P=O (6) | Cr(CO)$_6$ (1) | 2.68 |
| 10 | NiCl$_2$.6H$_2$O (2) | 45 | (C$_6$H$_5$)$_3$P=O (12) | Cr(CO)$_6$ (2) | 2.80 |
| 11 | NiCl$_2$.6H$_2$O (4) | 90 | (C$_6$H$_5$)$_3$P=O (4) | Cr(CO)$_6$ (4) (C$_4$H$_9$)$_4$NI (10) | 3.18 |
| 12 | NiCl$_2$.6H$_2$O (1) | 90 | (C$_6$H$_5$)$_3$P=O (12) | W(CO)$_6$ (1) (C$_6$H$_5$)$_3$P (5) | 1.9 |
| 13 | NiCl$_2$.6H$_2$O (1) | 35 | (C$_6$H$_5$)$_3$P=O (12) | W(CO)$_6$ (1) (C$_6$H$_5$)$_3$P (5) NaI (36) | 2.8 |

TABLE B

| Test No. | Methyl acetate (mmol) | CH$_3$I (mmol) | Promoter (mmol) | Co-promoter (mmol) | P$_{CO}$/P$_{H2}$ (bar) | gAc$_2$O/g Ni/g I/hour |
|---|---|---|---|---|---|---|
| 1 | 657 | 90 | (C$_6$H$_5$)$_3$P=O (4) | — | 20/20 | <0.01 |
| 2 | 262 | 50 | — | NMP* (339) | 20/20 | 0.9 |
| 3 | 262 | 35 | — | NMP (339) NaI (36) | 26⅜/13⅛ | 0.5** |
| 4 | 262 | 50 | (C$_6$H$_5$)$_3$P=O (4) | NMP (339) | 20/20 | 1.5 |
| 5 | 262 | 35 | (C$_6$H$_5$)$_3$P=O (12) | NMP (339) NaI (36) | 26⅜/13⅛ | 5.3** |
| 6 | 262 | 35 | (C$_8$H$_{17}$)$_3$P=O (12) | NMP (339) NaI (36) | 20/20 | 3.2*** |
| 7 | 262 | 25 | (C$_6$H$_5$)$_3$P=O (12) | NMP (339) LiI.2H$_2$O (36) | 26⅜/13⅛ | 8.66 |

*NMP = N—methylpyrrolidone
**1 hour reaction time
***4 hours reaction time

TABLE C

| Test No. | CH$_3$I (mmol) | Promoter (mmol) | Co-promoter (mmol) | g Ac$_2$O/g Ni/g I/hour |
|---|---|---|---|---|
| 1 | 15 | — | NMP (56.5) LiI.2H$_2$O (15) | 5.6 |
| 2 | " | (C$_6$H$_5$)$_3$P = O (6) | " | 15.5 |
| 3 | " | (C$_6$H$_5$)$_3$P = O (15) | " | 24.5 |
| 4 | 7.5 | (C$_6$H$_5$)$_3$P = O (30) | NMP (56.5) LiI.2H$_2$O (15) | 32.2 |

EXAMPLE IV

In the manner described in Example I, 25 ml methyl acetate were carbonylated at 180° C. in the presence of 1 mmol NiCl$_2$.6H$_2$O, 15 mmol CH$_3$I, 15 mmol LiI.2H$_2$0, 25 mol sulfolane and 6 mmol triphenylphosphine oxide. The partial CO and H$_2$ pressures before the autoclave was heated measured 30 and 15 bar, respectively. After a reaction time of 2 hours the reaction mixture was analyzed with the aid of gas-liquid chromatography. It was found that the acetic anhydride had been formed at a rate of 16.4 g Ac$_2$O/g Ni/g I/hours.

When the test was repeated with the triphenylphosphine oxide omitted, the rate at which the acetic anhydride was formed was 7.3 g Ac$_2$)O/g Ni/g I/hour, which indicates that triphenylphosphine oxide can still exercise intense promoter activity even when a sulphone is present.

EXAMPLE V

In the manner described in Example I, 25 ml methyl acetate were carbonylated at 165° C. in the presence of 2 mmol NiCl$_2$.6H$_2$O, 15 mmol CH$_3$I, 15 mmol LiI.2-H$_2$O, 25 ml sulfolane and 12 mmol triphenylphosphine oxide. The partial CO and H$_2$ pressures before the autoclave was heated each measured 20 bar. After a reaction time of 3 hours the reaction mixture was analyzed with the aid of gas-liquid chromatography. It was found that the acetic anhydride had been formed at a rate of 4.6g Ac$_2$O/g Ni/g I/hour. Comparison of this result with that of the first test of Example IV demonstrates that with a 10° C. temperature rise the reaction rate is approximately doubled.

EXAMPLE VI

In the manner described in Example I, 50 ml methyl acetate were carbonylated at 165° C. in the presence of 4 mmol NiCl$_2$.6H$_2$O, 90 mmol CH$_3$I, 12 mmol triphenylphosphine oxide and, as co-promoters, triphenylphosphine and certain metal compounds. Before the autoclave was heated, the partial CO and H$_2$ pressures were each 20 bar. The results are summarized in Table D.

TABLE D

| Test No. | Co-promoter | | Reaction time (hours) | g Ac$_2$O/g Ni/g I/hour |
|---|---|---|---|---|
| 1 | W(CO)$_6$ (C$_6$H$_5$)$_3$P | (4 mmol) (5 mmol) | 1 | 2.0 |
| 2 | ZrOCl$_2$.8H$_2$O (C$_6$H$_5$)$_3$P | (4 mmol) (10 mmol) | 1.5 | 2.7 |
| 3 | VCl$_3$ (C$_6$H$_5$)$_3$P | (4 mmol) (10 mmol) | 1.5 | 3.1 |
| 4 | FeCl$_2$ (C$_6$H$_5$)$_3$P | (4 mmol) (10 mmol) | 2 | 2.1 |
| 5 | didymium oxide (C$_6$H$_5$)$_3$P | (1 g) (10 mmol) | 2 | 1.9 |
| 6 | tetrabutyltin | (4 mmol) | 2 | 2.0 |

TABLE D-continued

| Test No. | Co-promoter | | Reaction time (hours) | g Ac₂O/g Ni/g I/hour |
|---|---|---|---|---|
| | (C₆H₅)₃P | (10 mmol) | | 5 |

I claim:

1. Process for the preparation of a carboxylic anhydride by reacting under virtually water-free conditions an ester having the formula $R^1COOCH_2R^2$ or an ether having the formula $R^3OR^4$ in which $R^1$, $R^3$ and $R^4$ represent hydrocarbon groups containing up to 20 carbon atoms and which may be substituted with halogen atoms, and $R^2$ represents hydrogen or a hydrocarbon group containing up to 20 carbon atoms and which may be substituted with halogen atoms; with carbonmonoxide in the presence of a nickel catalyst, an iodide and/or bromide source and at least one co-promoter, the improvement comprising that the reaction is carried out in the presence of: (A) a compound having the formula

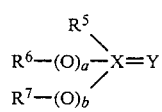  I in which X represents phosphorus, arsenic or antimony and Y oxygen, sulphur or selenium and a and b are 0 or 1 and $R^5$ represents hydrogen or a hydrocarbon group containing up to 30 carbon atoms which may be substituted with halogen atoms and $R^6$ and $R^7$ represent a hydrocarbon group containing up to 30 carbon atoms which may bear substituent selected from the group consisting of halogen atoms, and a $R^9R^{10}X=Y$ group wherein X and Y are defined above and $R^9$ and $R^{10}$ represent a hydrocarbon group containing up to 8 carbon atoms, or a and b are 0 and $R^6$ and $R^7$ together form a heterocyclic group with X, and $R^5$ is as defined above; or (B) in the presence of a complex of a compound having the formula I with a hydrocarbon iodide or bromide, an acyl iodide or bromde or HI or HBr.

2. Process in claim 1, wherein the hydrocarbon groups $R^1$, $R^2$, $R^3$ and $R^4$ are alkyl, cycloalkyl, aryl, alkaryl or aralkyl groups containing up to 12 carbon atoms.

3. Process as in claim 1, wherein the iodide and/or bromide source is selected from the group consisting of elementary iodine, elementary bromine, hydrogen iodide, hydrogen bromide and $R^8I$, $R^8Br$, $R^8COI$ or $R^8COBr$ compounds in which $R^8$ represents either an alkyl group which may be substituted with bromine or iodine, or an aralkyl group having not more than 12 carbon atoms.

4. Process as in claim 1, wherein the total number of gramatoms I and/or Br present in the reaction mixture lies between 1 and 500 gram-atoms I and/or Br per gram-atom Ni.

5. Process as in claim 1, wherein the catalyst contains as copromoter one or more compounds of metals in the groups IA, IIA, IIIA, IVA, IVB, VB, VIB and VIIB and/or of the non-noble metals in group VIII of the "Periodic System" and/or of metals in the lanthanides group and/or one or more organophosphorus compounds and/or organonitrogen compounds in which the phosphorus or nitrogen is trivalent and/or quaternary salts of said phosphorus or nitrogen compounds.

6. Process as in claim 5, wherein said co-promoter is a compound of a metal selected from the group consisting of a lithium, sodium, didymium, zirconium, vanadium, chromium, tungsten, manganese, iron and tin.

7. Process as in claim 5, wherein said co-promoter is an iodide or bromide of a group IA metal.

8. Process as in claim 5, wherein said co-promoter is a carbonyl compound of a group VIB metal.

9. Process as in claim 1, wherein said co-promoter is an alkyl-, cycloalkyl-, aryl-, or aralkylphosphine having not more than 30 carbon atoms.

10. Process as in claim 1, wherein said co-promoter is selected from the group consisting of an alkyl-, cycloalkyl-, aryl-, or aralkylamine having not more than 30 carbon atoms; a nitrile or a heterocyclic amine having not more than 14 carbon atoms; and an amide having not more than 14 carbon atoms.

11. Process as in claim 10, wherein said amide is N-methylpyrrolidone.

12. Process as in claim 5, wherein said co-promoter is a salt of a phosphine or amine with HI, HBr or an alkyl halide.

13. Process as in claim 1, wherein the hydrocarbon groups $R^5$, $R^6$ and $R^7$ are selected from the group consisting of alkyl-, cycloalkyl-, aryl-, aralkyl or alkaryl groups.

14. Process as in claim 1, wherein $R^6$ and $R^7$ together form a heterocyclic group with X and said heterocyclic group contains not more than 20 carbon atoms.

15. Process as in claim 1, wherein the compound of formula I, a and b are O, X is phosphorus and Y oxygen or sulphur and $R^5$, $R^6$ and $R^7$ represent alkyl groups having 1–12 carbon atoms or cycloalkyl, aryl, aralkyl or alkaryl groups having 5–12 carbon atoms.

16. Process as in claim 15, wherein Y is oxygen and $R^5$, $R^6$ and $R^7$ represent alkyl groups having 1–12 carbon atoms or phenyl groups.

17. Process as in claim 1, wherein the amount of compound having the formula I used is between 0.1 and 100 mols per gram-atom nickel.

18. Process as in claim 1, wherein the reaction is carried out at a temperature from about 100° to about 200° C.

19. Process as in claim 1, wherein the partial pressure of the carbon monoxide is from about 0.5 to about 50 bar.

* * * * *